United States Patent [19]

Zweifel

[11] Patent Number: 5,365,783
[45] Date of Patent: Nov. 22, 1994

[54] CAPACITIVE SENSING SYSTEM AND TECHNIQUE

[75] Inventor: Ronald A. Zweifel, Naperville, Ill.

[73] Assignee: Packard Instrument Company, Inc., Downers Grove, Ill.

[21] Appl. No.: 55,538

[22] Filed: Apr. 30, 1993

[51] Int. Cl.$^5$ .............................................. G01F 23/26
[52] U.S. Cl. ................... 73/304 C; 324/662; 324/663
[58] Field of Search .............. 73/304 C; 324/662, 663

[56] References Cited

U.S. PATENT DOCUMENTS

| | | | |
|---|---|---|---|
| 3,862,571 | 1/1975 | Vogel | 73/304 C |
| 3,864,974 | 2/1975 | Rauchwerger | 73/304 C |
| 3,901,079 | 8/1975 | Vogel | 73/304 C |
| 4,165,641 | 8/1979 | Pomerantz et al. | 73/290 R |
| 4,482,891 | 11/1984 | Spencer | 73/304 C |
| 4,603,581 | 8/1986 | Yamanoue et al. | 73/304 C |
| 4,736,638 | 4/1988 | Okawa et al. | 73/304 C |
| 4,818,492 | 4/1989 | Shimizu | 73/863.02 |
| 4,833,393 | 5/1989 | Wetzel | 324/60 SD |
| 4,875,497 | 10/1989 | Worthington | 73/304 C |
| 5,001,927 | 3/1991 | LaCava et al. | 73/304 C |
| 5,005,407 | 4/1991 | Koon | 73/290 R |
| 5,045,797 | 9/1991 | Kramer et al. | 324/671 |
| 5,065,139 | 11/1991 | Shefsky | 340/620 |
| 5,083,470 | 1/1992 | Davis et al. | 73/864.24 |

FOREIGN PATENT DOCUMENTS

| | | | |
|---|---|---|---|
| 4118170 | 12/1992 | Germany | 73/304 C |
| 0087425 | 5/1983 | Japan | 73/304 C |
| 2225223A | 10/1989 | United Kingdom | |
| 8810412 | 12/1988 | WIPO | 73/304 C |

*Primary Examiner*—Diego F. F. Gutierrez
*Attorney, Agent, or Firm*—Arnold, White & Durkee

[57] ABSTRACT

An arrangement senses a liquid level by monitoring the peak capacitance formed between a probe and the liquid as the probe approaches or departs from the liquid. In an automated system, a computer controls the position of a pipette probe for aspirating or dispensing liquid in the vessel. The charge developed via the capacitance on the probe is coupled to a capacitive sensor circuit which provides a peak detector with an amplified signal representing the peak capacitance between the probe and the liquid. This amplified signal is detected by a peak-capacitance discrimination circuit, the output of which is monitored by the computer for determining the precise position of the probe with respect to the liquid surface level. Other aspects of the present invention include a negative-static elimination circuit coupled to the output of a detector latch and a positive-static elimination circuit coupled to the input of the detector latch.

10 Claims, 5 Drawing Sheets

CAPACITIVE SENSING SYSTEM AND TECHNIQUE

FIELD OF THE INVENTION

The present invention relates generally to capacitive liquid level sensors and, more particularly, to liquid-level sensing systems measuring capacitance between a probe and liquid to be deposited or withdrawn from a vessel.

BACKGROUND OF THE INVENTION

Withdrawing and dispensing precise volumes of liquid without contaminating the liquid is a large and important part of many clinical applications and laboratory tests. While attempts to address these applications and tests manually have failed to provide the needed accuracy and purity, a number of automated or semi-automated liquid-measuring systems are presently being used to gauge more precisely the small liquid volumes to be withdrawn and/or dispensed in such applications and tests.

One of the more popular types of liquid-measuring systems uses motor-controlled pipette-like probes to aspirate or dispense a desired amount of fluid from or into a vessel. The probes are movably mounted over the vessel and, using a precision-controlled motor, are lowered into the vessel until the tip of the probe reaches a desired level below or above the upper surface of the liquid, or meniscus. A desired amount of liquid is then withdrawn from or dispensed into the vessel. Such systems have been designed with the goals of: minimizing cross-contamination between the contents of different vessels, avoiding splashing the liquid during the aspiration (deposition) process, and minimizing the portion of the probes that must be washed.

For example, liquid-measuring systems have been developed which require a vessel to be filled to a predetermined level, so that the pipette-like probe can be lowered to a predetermined position with the expectation that the probe has been precisely positioned with respect to the predetermined level. Unfortunately, such systems are disadvantaged, because the step of filling the vessel to a predetermined level is laborious, seldom precise and, when there is a limited volume of liquid available, sometimes impossible.

More recently developed liquid-measuring systems of this type control the position of the probe tip without previously knowing the upper level of the liquid in the vessel. This is accomplished by searching for the upper level of the liquid in the vessel as the probe tip is lowered into the vessel. By measuring some electrical phenomena associated with a change in the capacitance between the probe and the liquid in the vessel as the tip of the probe approaches the liquid, the system can then position the probe tip without the disadvantageous step of precisely establishing liquid at a predetermined level in the vessel. These systems typically search for the upper level of the liquid by sensing when the capacitance between the probe and the liquid reflects a change in voltage level that is greater than a threshold reference level.

A problem with this technique is that is dependent upon the sensitivity of the system's electronics monitoring the change in voltage level. If this sensitivity is inferior or degrades over time, the sensed voltage level change will be skewed and the system will be unable to compare accurately the change in voltage level to the threshold reference level. Further, an inferior or degraded ability to sense the change in voltage level results in delayed detection of the liquid level, which can cause the system to lower the probe beyond the desired level. This can result in contamination, splashing, etc., as previously discussed.

Another problem with this technique is that the sensed change in voltage level may not reach the threshold reference level in applications using, for example, small liquid volumes or certain types of liquids. Systems using a fixed threshold level are incapable of dealing with these applications, and systems providing the ability to adjust the threshold level require a laborious calibration process.

A previously unaddressed problem, which is believed to have been discovered in connection with the present invention, concerns unexpected capacitance-level changes in systems using multiple pipette-type probes for handling multiple liquid vessels. In applications using multiple probes to test the various liquid vessels, a capacitance change between one probe and its associated liquid vessel can significantly affect the capacitance between another of the probes and its associated liquid vessel. If not avoided, this seriously undermines the integrity of the operation involving the affected liquid vessel.

Accordingly, there is a need for a liquid-level sensing system, capable of precisely measuring capacitance between a probe and liquid, that can be implemented without the aforementioned shortcomings.

SUMMARY OF THE INVENTION

Generally, the present invention provides a liquid-level sensing system, capable of precisely measuring capacitance between a probe and liquid, which overcomes the above-discussed deficiencies.

More specifically, the present invention provides an arrangement for sensing a liquid level by monitoring the peak capacitance formed between a probe and the liquid as probe approaches or departs from the liquid. In an automated system, a computer controls the position of a pipette probe for aspirating or dispensing liquid in the vessel. The charge developed via the capacitance on the probe is coupled to a capacitive sensor circuit which provides a peak detector with an amplified signal representing the peak capacitance between the probe and the liquid. This amplified signal is detected by a peak-capacitance discrimination circuit, the output of which is monitored by the computer for determining the precise position of the probe with respect to the liquid surface level.

In another preferred embodiment, the above-summarized arrangement includes the probe being coupled to the capacitive sensor circuit using the inner and outer conductors of a coaxial cable. The capacitive sensor circuit includes an operational amplifier with one input coupled to the probe and the inner conductor of the cable and with the second input of the operational amplifier coupled to the outer conductor of the cable. The outer conductor acts as a driven shield to cancel the undesired capacitances in the cable.

A static charge eliminator circuit, for eliminating the effect of positive and negative static charges conducted from the vessel to the probe, can be used with the discrimination circuit to eliminate false peaks that would otherwise be sensed by the computer.

In still another preferred embodiment, a capacitive liquid level sensor system for determining the level of liquid in a plurality of vessels in an automated pipetting system comprises a plurality of pipette probes for aspirating or depositing liquid in the vessels. Each of the probes is automatically controlled using one of the above-described capacitive sensing circuits, and using a plurality of switches to sequentially enable a charge to be developed via the capacitance on each probe.

The above summary of the present invention is not intended to represent each embodiment, or every aspect, of the present invention, as this is the purpose of the figures and the detailed description which follow.

BRIEF DESCRIPTION OF THE DRAWINGS

Other objects and advantages of the invention will become apparent upon reading the following detailed description and upon reference to the drawings in which.

While the invention is susceptible to various modifications and alternative forms, specific embodiments thereof have been shown by way of example in the drawings and will be described in detail. It should be understood, however, that it is not intended to limit the invention to the particular form described. On the contrary, the intention is to cover all modifications, equivalents and alternatives falling within the spirit and scope of the invention as defined by the appended claims.

DETAILED DESCRIPTION OF THE PREFERRED EMBODIMENTS

Figure 1:
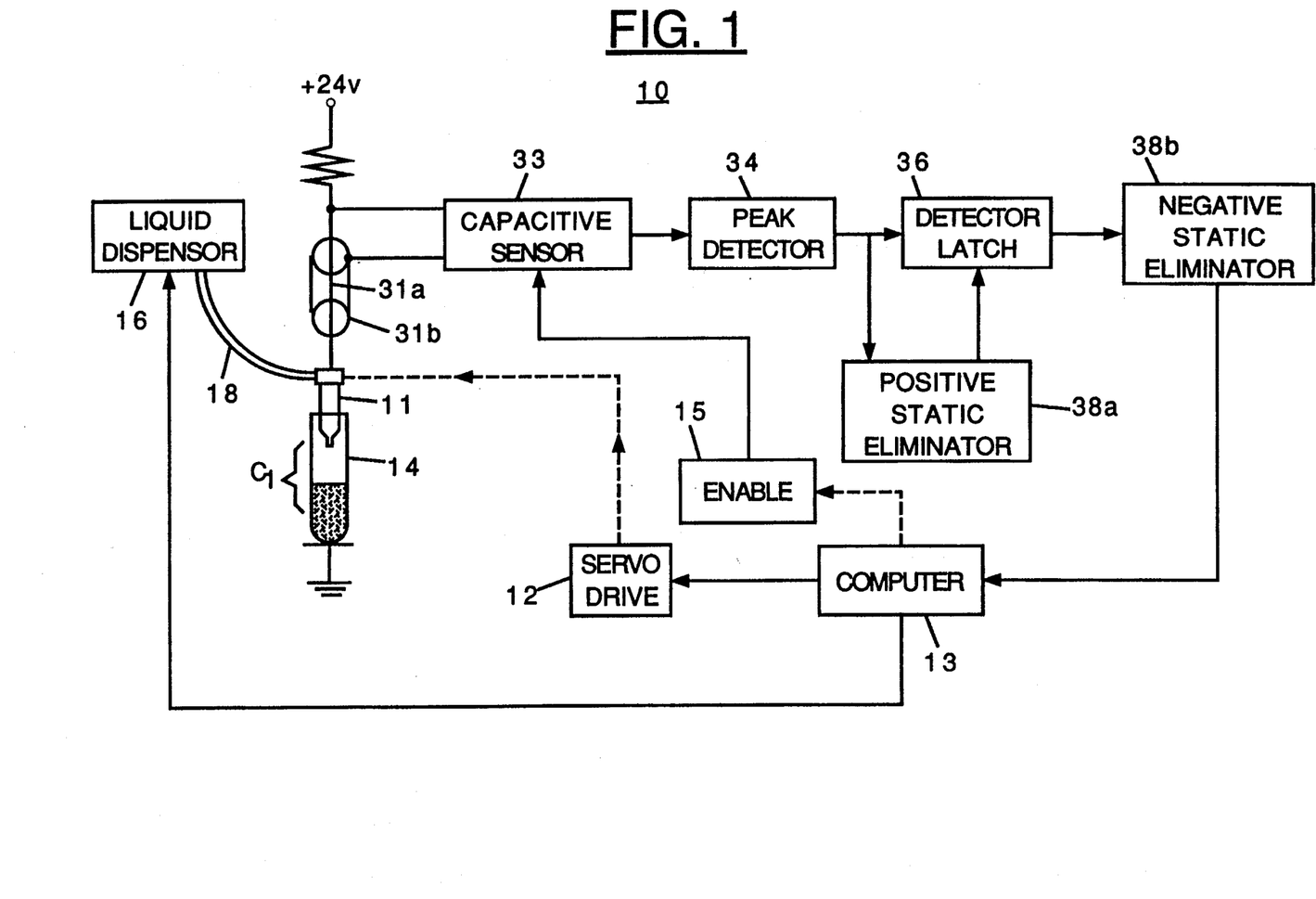
FIG. 1 is a block diagram of a capacitive sensing system, in accordance with the present invention, controlling a single probe with respect to liquid in a laboratory vessel.

FIG. 1 illustrates a preferred embodiment of a capacitive sensing system 10 which, in accordance with the present invention, provides optimal control over the position of a probe 11 with respect to an unknown level of liquid in a conventional laboratory vessel 14. Movement of the probe 11 into or out of the vessel 14 is controlled by a conventional servo-drive 12, which in turn is controlled by a microcomputer or CPU 13. The CPU 13 determines the precise position of the probe 11, with respect to the level of the liquid in the vessel 14, by closely monitoring a processed signal 15 representing the peak stray capacitance between the probe 11 and the liquid in the vessel 14. The CPU may also be programmed to control a liquid dispenser 16 which passes liquid from or to the probe 11 via a flexible tube 18 made from a chemically inert material such as Teflon.

The stray capacitance, depicted as $C_1$, between the probe 11 and the liquid in the vessel 14 slowly increases as the probe 11 is moved toward the liquid. When the probe contacts the liquid in the vessel 14, the stray capacitance increases virtually instantaneously. The capacitive sensing system 10 couples this stray capacitance, via a driven shield 31a, b, so that a peak detector 34 and a detector latch 36 can inform the CPU 13 of the exact time at which the probe contacts the liquid in the vessel 14.

The stray capacitance $C_1$ is monitored by momentarily applying a voltage to the capacitance $C_1$ and coupling the voltage charge on the capacitance $C_1$ to the peak detector 34, which detects the peak voltage developed on the capacitance $C_1$. When the probe contacts the liquid, the rapid increase in the stray capacitance increases cause the voltage of the capacitance to decrease rapidly. This decreased signal level does not change as long as the probe remains in the liquid. The peak detector 14 senses this rapid decrease in voltage and the detector latch 36 latches this signal at its output.

More specifically, the voltage is applied to the capacitance $C_1$ only momentarily, e.g., for about 14 microseconds, using a switch-like enabler circuit 15 to permit an AC Voltage divider circuit, which is sourced from a $V_{DC}$ signal (+24 V) and coupled through $C_1$ to earth ground at the vessel 14, to momentarily charge the capacitance $C_1$ to about 14 volts. When the 12 microsecond period ends and as the probe is moved toward (or away) from the liquid, the capacitance $C_1$ increases (decreases) and causes the voltage charge at the capacitance $C_1$ to decrease (increase). When the capacitance $C_1$ peaks, the voltage charge at the capacitance $C_1$ peaks in the opposite direction. In the situation in which the probe is approaching the liquid, for example, the capacitance $C_1$ reaches its maximum level, causing the voltage charge at the capacitance $C_1$ to decrease virtually instantaneously.

The voltage charge at the capacitance $C_1$ is coupled to the peak detector 34 using a driven shield 31b, which is preferably implemented using a coaxial cable 31b. With the inner conductor 31a of the coaxial cable electrically connected as part of the AC voltage divider circuit, the voltage charge on the capacitance $C_1$ is coupled to the outer conductor 31b of the coaxial cable and buffered and amplified by a capacitive sensor 33. The peak detector 34 receives this buffered and amplified signal directly from the output of the capacitive sensor 33.

Figure 2:
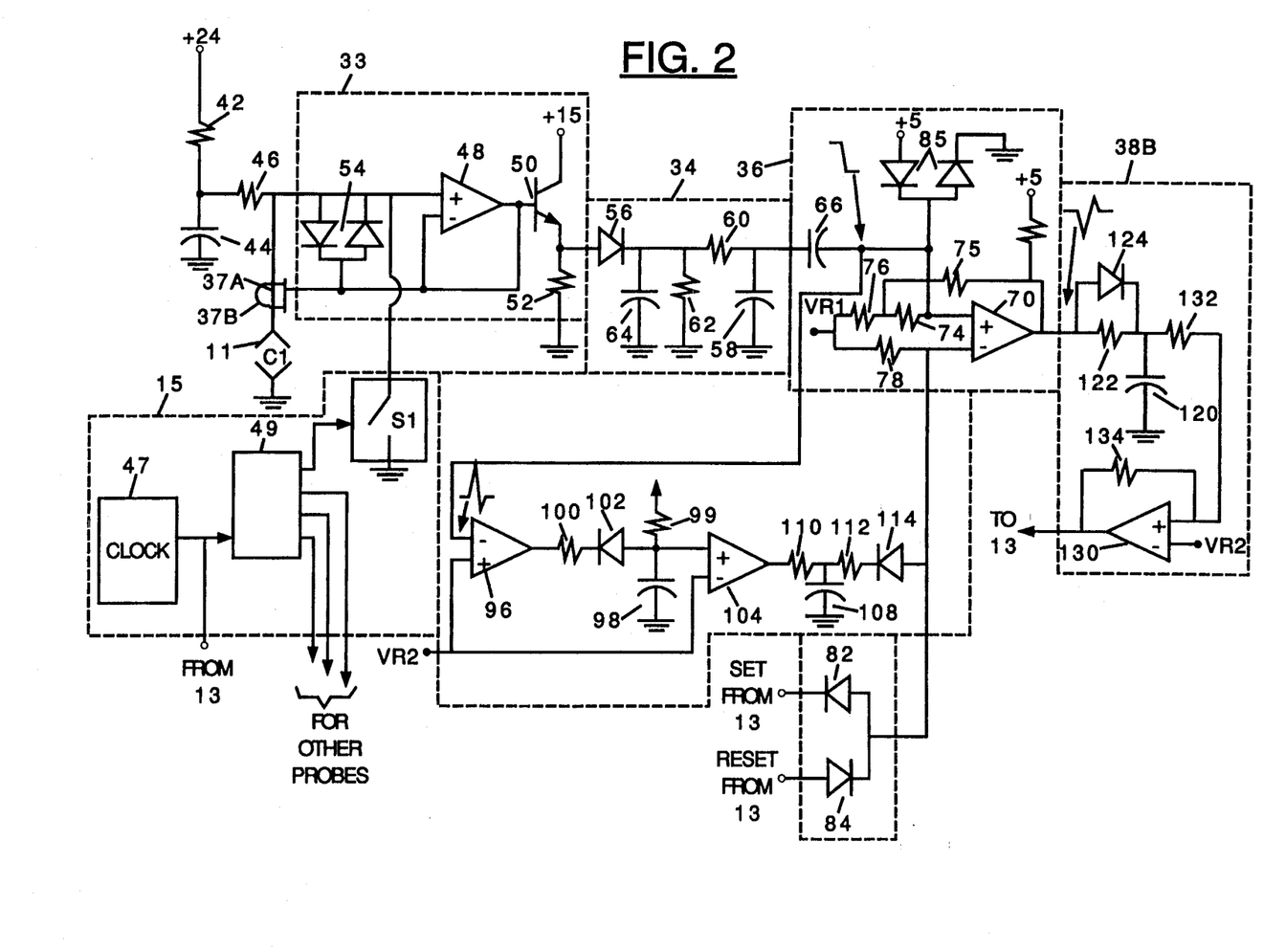
FIG. 2 is a schematic diagram showing a preferred implementation of the capacitive sensing system shown in the block diagram of FIG. 1.

The dotted lines connecting the computer 13 to the enabler 15 in FIG. 1 are used to help illustrate that the enabler is activated using a manually controlled switch (not shown), using self contained circuitry (e.g., as shown in FIG. 2), or under control of the computer 13.

Another important aspect of the present invention concerns the problem of static electricity, initially on or near the vessel 14, being coupled into the capacitive sensing system 10. Typically, the static electricity arcs onto the probe 11 as the probe 11 moves with respect to the vessel 14. If this static electricity is coupled into the system, it will cause an instantaneous change in the capacitance $C_1$, causing a false peak voltage signal to be detected by detector latch 36. To avoid this problem, a positive static eliminator 38a and a negative static eliminator 38b are coupled to the respective input and output of the detector latch 36. These static eliminators can be included as part of the discrimination circuit provided by the detector latch 36, to remove such static charges so as to avoid a false reading by the system 10. The above discrimination circuit shown in FIG. 1 is not implemented in this instance using a programmed microcomputer.

FIG. 2 illustrates the system 10 in more detail. The AC voltage applied to the capacitance $C_1$ between the probe 11 and the liquid is provided using an AC voltage divider circuit, which is sourced by a +24 volt supply signal and is terminated via the earth-grounded vessel (14 of FIG. 1). The AC voltage divider circuit includes a resistor 42 feeding in series a capacitor 44 in parallel with a series circuit comprising a resistor 46 and the capacitance $C_1$. The enabler 15 includes a switch S1, which is activated via a period clock signal generated by a clock circuit 47 (such as 555-type timer or monostable vibrator). The clock circuit 47 provides a control signal to a sequencer (or counter chip) 49 which, in turn, generates a timed control signal to close the contacts of the switch S1 for about 14 microseconds and at a rate of about 70 kHz. Three other outputs from the sequencer 49 are used when this system 10 is repeated to control similarly arranged switches S1 for the operation of multiple probes, as discussed infra in connection with FIGS. 3 and 4.

The junction between the resistor 46 and the capacitance $C_1$ is connected to the positive input terminal of an operational amplifier 48 with its output fed back to its negative input and connected directly to the outer conductor 31b of the coaxial conductor 31. This arrangement provides the sensitive voltage on the probe 11, in amplified form, to the base of a driving transistor 50 which, using a bias resistor 52 at its emitter, drives the input of the peak detector 34. Furthermore, by connecting the inner conductor 31a to the positive input and the outer conductor 31b to the negative input of the operational amplifier 48, the arrangement acts as a driven shield to cancel the capacitive effect between the inner and outer conductors of the cable 31. Diodes 54 are used to cancel transients at the inputs of the operational amplifier 48.

The peak detector 34 is shown to be implemented using a passive resistor-capacitor charging circuit, with a blocking diode 56 preventing discharge via the bias resistor 52. In response to the switch S1 permitting a charge of about 12 volts to develop on the capacitance $C_1$, current provided by the transistor 50 slowly charges a capacitor 58 through a resistor 60, with the capacitor 58 and resistor 60 acting together as a low pass filter to filter out any transient signals. At the front side of the resistor 60, a shunting high pass filter (resistor 62 in parallel with capacitor 64) permits a slow discharge of the voltage developed on the capacitor 58 and shunts the spike resulting from the instantaneous change in stray capacitance $C_1$. The momentary presence of the spike at the left side of the resistor 60, however, is coupled to the detector latch 36 through an input coupling capacitor 66.

The detector latch 36 provides signal discrimination for detecting and latching, at the output of an operational amplifier 70, the signal coupled via the coupling capacitor 66. The operational amplifier 70, which includes a positive input connected to the detector latch side of the coupling capacitor 66, is voltage sensitive with equal hysteresis for positive or negative instantaneous changes in voltage. The latching and hysteresis functions are provided by a resistive feedback path (resistor 75) from the output of the operational amplifier 70 to its positive input. Using a reference voltage $V_{R1}$ to bias, via resistors 76, 74 and 78, both the positive and negative inputs to the operational amplifier 70, the operational amplifier compares the signal at the positive input port with the reference voltage $V_{R1}$ to determine when to latch the input signal at the output.

Another important part of the discrimination process at the detector latch concerns the negative input to the operational amplifier 70. This input is "OR" tied through respective diodes 82 and 84 with a pair of computer control signals, RESET and SET, to allow the computer to disable the detector latch 36 until just before the computer expects the probe to meet the top of the liquid. By programming the computer with a level of reference to the top of the vessel, the RESET and SET signals can be used to ensure that the detector latch is not activated for improper reasons. In one embodiment, for example, the computer is programmed to change the RESET signal to a low state (ground) as the probe is moving toward the liquid, forcing the output of the amplifier 70 to its proper (normal high) state regardless of the condition at the input.

A diode pair 85 serves as an input protector to prevent an unusually large signal coupled through the capacitor 66 from damaging the amplifier 70.

Further signal discrimination is provided by coupling the static eliminators 38a and 38b to the respective input and output ports of the detector latch 36. The positive static eliminator 38a is used to reset the amplifier 70, as described in connection with the RESET signal, but in response to a pulse of undesired positive static electricity being coupled across the capacitor 66 and to an operational amplifier 96. The output of the operational amplifier 96 is normally high, permitting a capacitor 98 to be fully charged to +5 volts through a resistor 99. However, in response to such a positive static signal being above a second reference voltage signal ($V_{R2}$), the operational amplifier 96 quickly discharges the capacitor 98 through a resistor 100 and a blocking diode 102 which, in turn forces the output of an operational amplifier 104 to its lowest level (essentially ground). This discharges a capacitor 108 through a resistor 110 and effects a RESET of the detector latch 36 through a resistor 112 and a blocking diode 114. The positive static signal effects a discharge of the capacitor 98 only for about four milliseconds, which is a period greater than the expected duration of the static signal. After four milliseconds, the resistor 99 sufficiently charges the capacitor 98 to force the output of the amplifier 104 to its normal high level. This is important because, as will be discussed, the static eliminator 38a blocks any signal-detection reporting to the computer unless the signal coupled across the capacitor 66 is present for about five milliseconds. Thus, the limited duration of the positive static pulse will not cause a false detection by the computer.

A discovery that is part of the present invention is the presence of small static charges of short duration, which can occur when the tip of the probe touches the liquid. This is unlike the normal static transfer, which arcs onto the probe. As an option, the resistor 100 can be located in the eliminator 38a to eliminate this problem. The value of the resistor 100 is selected so that small positive static charges of short duration, effect only a partial discharge of the capacitor 98. Consequently, the resistor 99 is able to sufficiently charge the capacitor 98 in a shorter time period, corresponding to the maximum time period needed to wait out the static pulse. When using this resistor 100, there is obviously this selected delay which offsets the reaction time before the computer learns of the contact with the liquid.

Thus, the value and/or use of the resistor 100 should be balanced against the offset of this reaction time.

The negative smile eliminator 38b, at the output of the detector latch 36, uses the small positive signal ripple immediately following the negative static signal to reset the amplifier 70 after the first part of the negative static signal causes the amplifier 70 to latch the input to the output. This operation of the detector latch 36, therefore, differs as when compared to it receiving the negative-going signal representing maximum stray capacitance at $C_1$, where the corresponding decreased voltage signal does not change as long as the probe remains in the liquid.

After the negative static signal resets the amplifier 70, the output of the amplifier 70 begins discharging a capacitor 120 through a resistor 122, together which set a time constant of about five milliseconds, as previously noted. The small positive signal tipple immediately following the negative static signal appears in less than four milliseconds, which forces the output of the amplifier 70 high and immediately charges the capacitor 120 to its normal level through a blocking diode 124. An amplifier 130, having a hysteresis set by resistors 132 and 134, reports the signal-detection to the computer, when the signal coupled across the capacitor 66 is present for about five milliseconds and the voltage on the capacitor 120 goes below a reference voltage $V_{R3}$ connected to the negative input terminal of the amplifier 130.

Accordingly, the positive static eliminator 38a uses a time-out circuit to reset the amplifier 70 until the expected duration of the positive static interference lapses, and the negative static eliminator 38a uses the small positive signal ripple immediately following the negative static signal to reset the amplifier 70.

When automatically controlling and operating multiple probes 11, the basic circuit represented in FIGS. 1 and 2 can be run in parallel, with the computer 13, the enabler 15 and voltage divider circuits for setting each of the reference voltages $V_{R1}$, $V_{R2}$ and $V_{R3}$ providing simultaneous control for each system 10A, 10B, 10C, 10D and with the exceptions that are discussed below.

Figure 3:
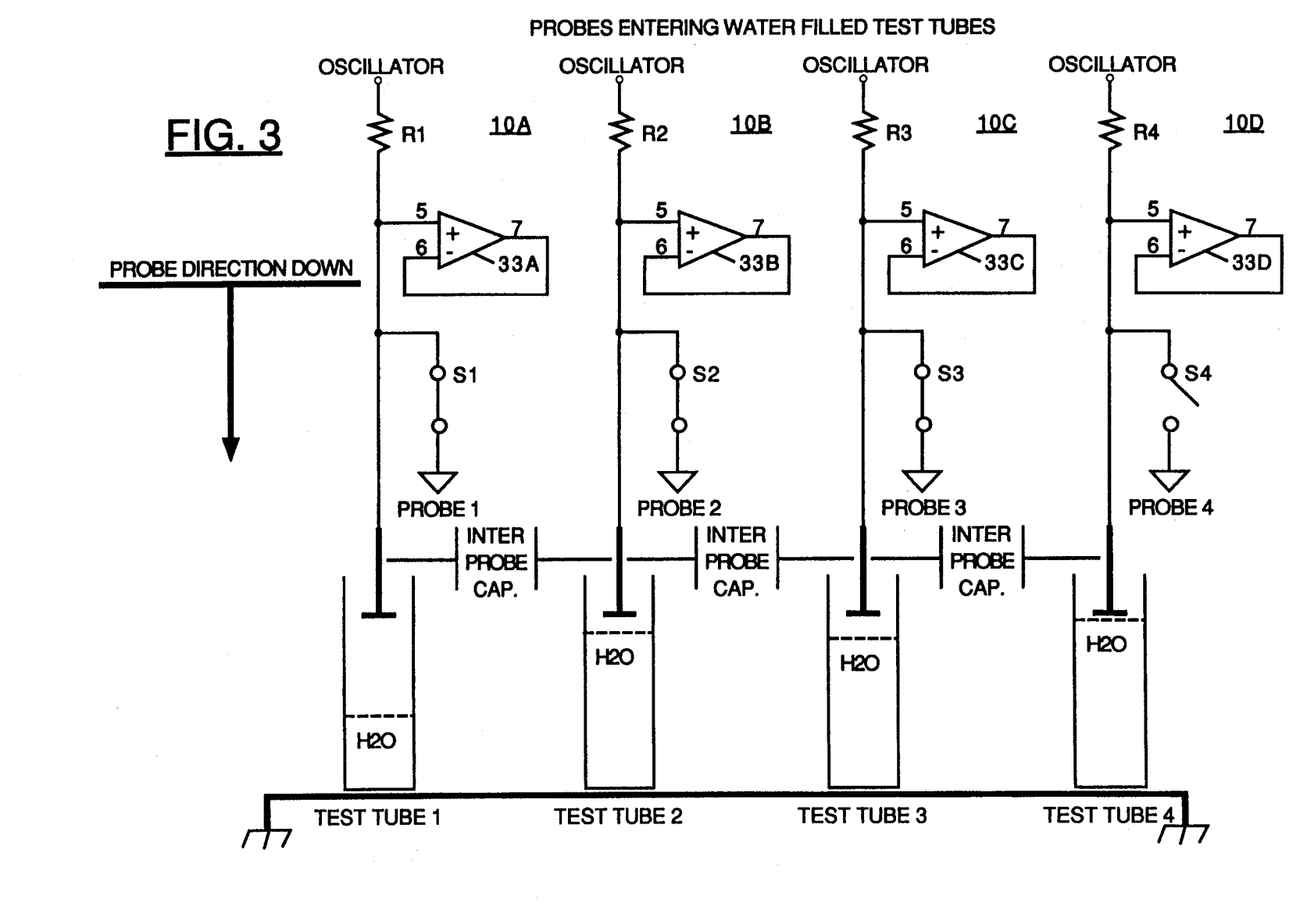
FIG. 3 is a block diagram representation of the insertion operation of a multi-probe embodiment of a capacitive sensing system, in accordance with the present invention.

Turning now to FIG. 3, a block diagram representation of the insertion operation of a multi-probe embodiment of the capacitive sensing system 10 (FIG. 1) is illustrated. Each of four systems 10a–10d is shown in abbreviated form to include the capacitive sensor 33 of FIG. 1 (shown in FIG. 3 as 33A, 33B, 33C and 33D), the switch S1, the probe (11 of FIGS. 1 and 2) and the vessel 14 with water contained therein. The problem illustrated in FIG. 3 is the transfer of charges via inter-probe capacitance when the probes are arranged relatively close to one another and when the liquid levels differ. In this situation, there is a risk that the first probe to contact (or leave) the liquid will transmit, e.g., via capacitance, the transient voltage change to one of the other active probes and cause a false detection of the liquid level. To overcome this potential problem, the probes are read one at a time using the enabler (clock and sequencer) to keep the switches S1 closed except for the one probe being lowered toward the liquid. In this manner, when a probe tip touches the liquid surface, its voltage change cannot affect the other probes. Alternatively, the nonadjacent probes may be operated simultaneously or in a non-contiguous manner (e.g., where there are five probes and switches: S1, S3, S5, S2, S4, S1, etc.).

Figure 4:
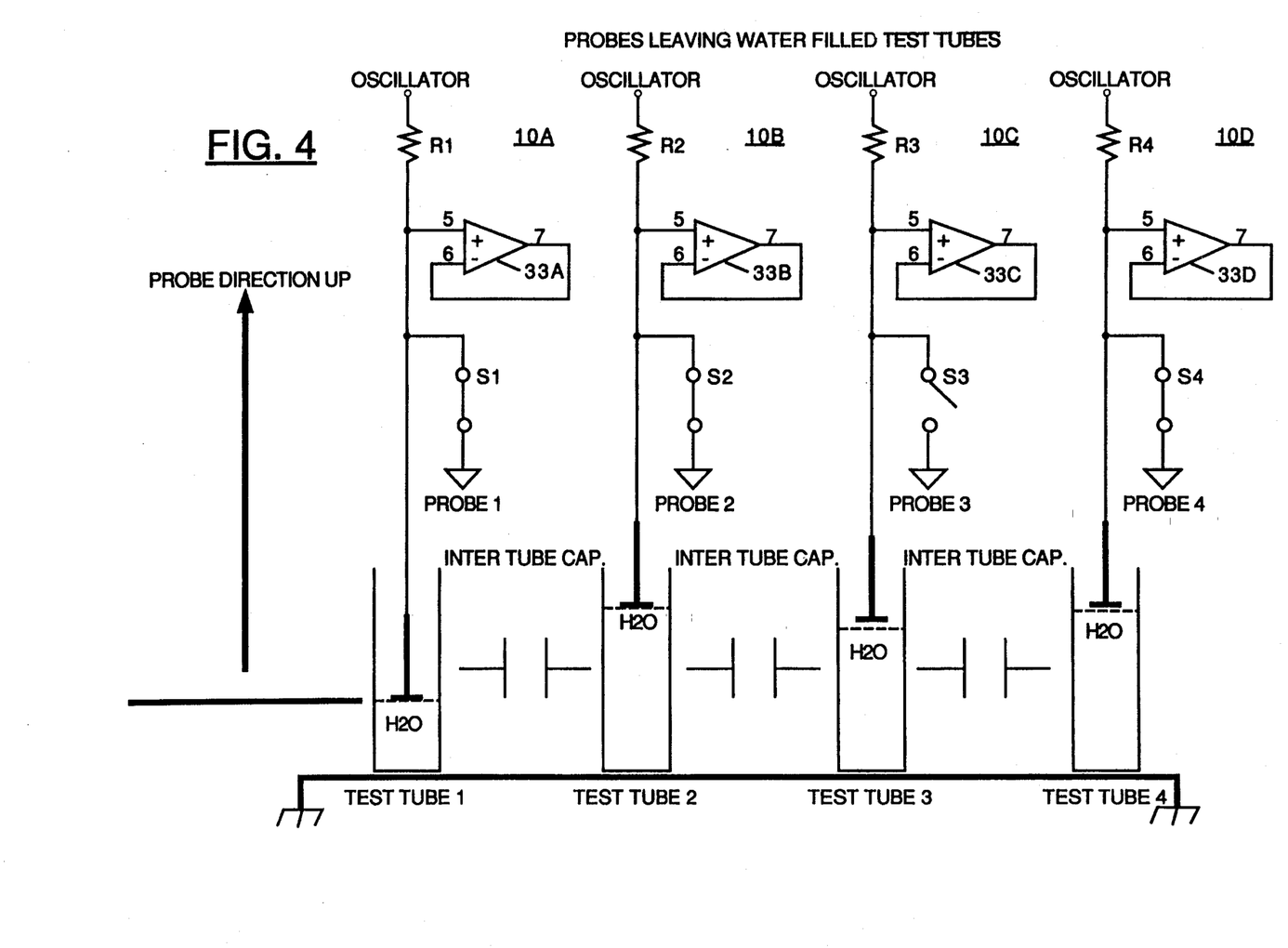
FIG. 4 is a block diagram representation of the extraction operation of a multi-probe embodiment of a capacitive sensing system, also in accordance with the present invention.

This sequential activation of the switches is not a total resolution when extracting the probes from the liquid because, as shown in FIG. 4, there is inter-vessel capacitance which will transfer the voltage change when the probe pulls free of the surface of the liquid. A preferred solution to this problem is to operate one probe at a time and to toggle its SET line (to the amplifier 70 of FIG. 2) just after the probes are withdrawn from the liquid, say 0.05 inch above the surface. This fine measurement is possible because the surface level was already determined (and stored in the computer's internal memory) when the probe was being inserted into the liquid. After toggling the SET line, the output of the amplifier 70 transits from normally high to low and the setting of the amplifier should not change again. The probe is then brought to its upper (home) position. This is repeated for each probe.

Figure 5:
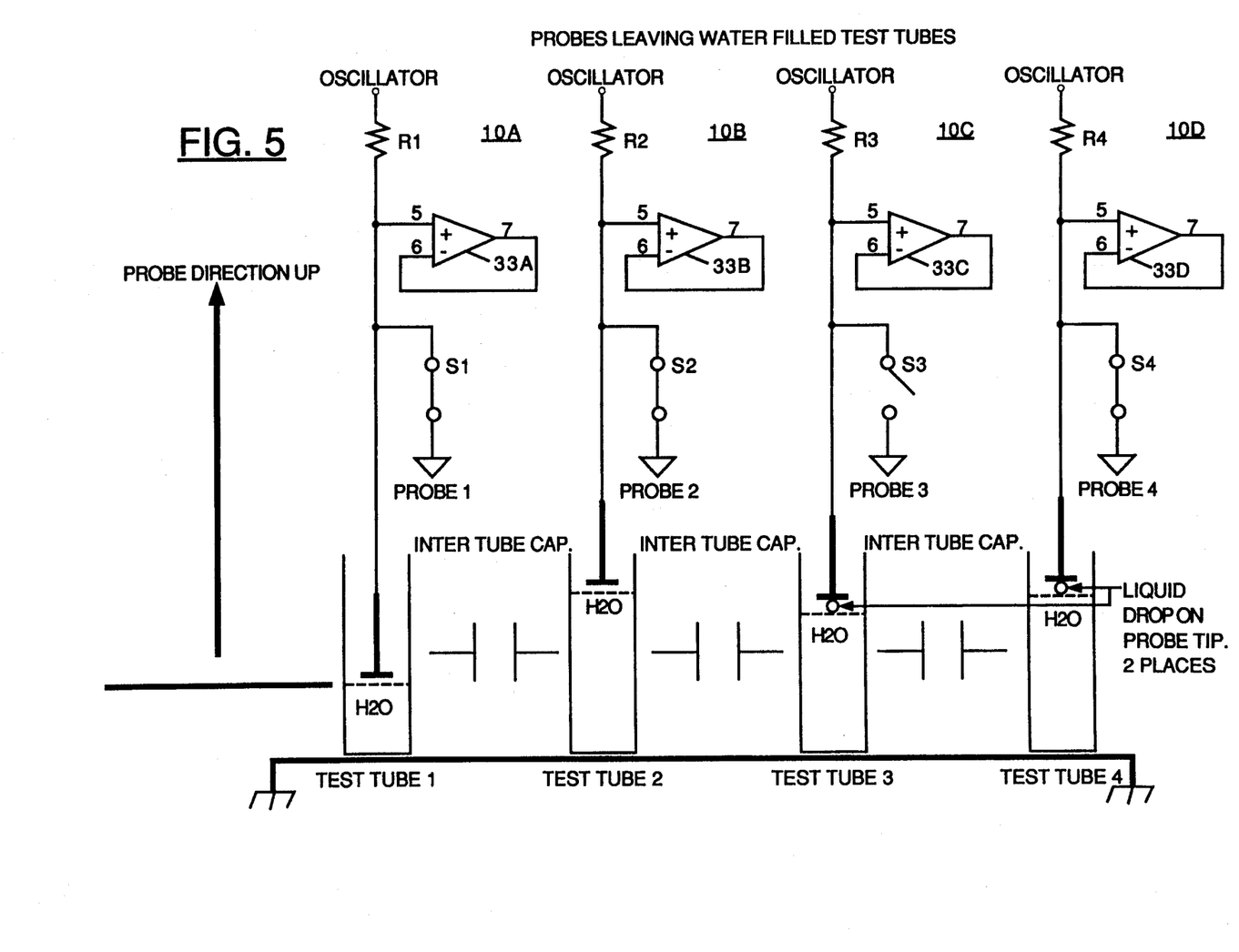
FIG. 5 is a block diagram showing basically the same inventive arrangement as shown in FIG. 4, except with drops at the tips of the third and fourth probes.

When the first probe clears the surface of the liquid, it will sense the capacitive change and clear the amplifier 70 as in a RESET. If any other probe was in the liquid at this time, its respective amplifier 70 may also have been reset due to inter-vessel capacitance but this does not matter because of the SET operation after removing each probe. If the state of the amplifier changes when the probe is completed retracted from over the liquid, then there is a drop (or clot) on the end of the probe which was maintaining contact between the probe and the liquid, as shown for probes 3 and 4 of FIG. 5, when the SET line was toggled. Consequently, the computer signals a failure for this probe.

Those skilled in the art will readily recognize that various modifications and changes may be made to the present invention without departing from the true spirit and scope thereof, which is set forth in the following claims.

What is claimed is:

1. A capacitive liquid level apparatus, comprising:
 a probe movably controllable over liquid in a vessel, the probe being constructed and arranged over the liquid to form a capacitance therebetween;
 a supply circuit coupled to said probe;
 a capacitive sensor coupled to the probe and arranged to provide an electrical signal representing the capacitance;
 a peak detection circuit sensing a peak magnitude in the electrical signal;
 a discrimination circuit providing a hysteresis control signal, the discrimination circuit, responsive to the peak detection circuit sensing said peak magnitude in the electrical signal and to the hysteresis control signal, determining a peak level corresponding to the peak magnitude and a level of liquid inside the vessel; and
 an automated control circuit movably controlling the probe in response to the discrimination circuit determining said peak level.

2. A capacitive liquid level apparatus, according to claim 1, further including a circuit arranged to selectively enable the capacitive sensor.

3. A capacitive liquid level apparatus, according to claim 1, further including a coaxial cable arranged to couple the capacitive sensor to the probe.

4. A capacitive liquid level apparatus, according to claim 3, wherein the coaxial cable includes an inner conductor and an outer conductor, the outer conductor arranged to cancel undesired capacitance in the cable.

5. A capacitive liquid level apparatus, according to claim 1, further including a circuit arranged to selectively enable the capacitive sensor and a coaxial cable arranged to couple the capacitive sensor to the probe.

6. A capacitive liquid level apparatus, according to claim 1, wherein the discrimination circuit is arranged to reduce deleterious effects of static charges at the probe from causing erroneous sensing of said peak magnitude.

7. A capacitive liquid level apparatus, according to claim 6, wherein the discrimination circuit is arranged to reduce the effects of positive static charges at the probe.

8. A capacitive liquid level apparatus, according to claim 6, wherein the discrimination circuit is arranged to reduce the effects of negative static charges at the probe.

9. A capacitive liquid level apparatus, according to claim 6, wherein the discrimination circuit is arranged to reduce the effects of positive and negative static charges at the probe.

10. A capacitive liquid level apparatus, according to claim 6, wherein the discrimination circuit is arranged without using a programmed microcomputer.

* * * * *